United States Patent [19]

Brouwer

[11] Patent Number: 5,583,056
[45] Date of Patent: Dec. 10, 1996

[54] METHOD FOR PREPARING AQUEOUS SUSPENSION FOR DIAGNOSTIC TESTS

[75] Inventor: Wilfridus M. Brouwer, NT Velp, Netherlands

[73] Assignee: Akzo Nobel N.V., Arnhem, Netherlands

[21] Appl. No.: 439,624

[22] Filed: May 12, 1995

Related U.S. Application Data

[62] Division of Ser. No. 865,773, Apr. 6, 1992, abandoned, which is a continuation of Ser. No. 731,373, Jul. 16, 1991, abandoned, which is a continuation of Ser. No. 434,965, Nov. 13, 1989, abandoned.

[30] Foreign Application Priority Data

Nov. 14, 1988 [NL] Netherlands ................. 8802783

[51] Int. Cl.$^6$ ................ G01N 33/551; G01N 33/553
[52] U.S. Cl. ........ 436/525; 252/62.54; 252/62.55; 252/310; 252/315.2; 427/212; 427/215; 427/216; 427/220; 428/402; 428/403; 428/406; 428/407; 436/524; 436/526; 436/528; 436/531; 436/532
[58] Field of Search ................ 427/212, 215, 427/216, 220; 428/402, 403, 406, 407; 252/62.54, 62.55, 310, 315.2; 436/518, 524, 525, 526, 528, 531, 532, 533, 534

[56] References Cited

U.S. PATENT DOCUMENTS

| | | |
|---|---|---|
| 4,157,323 | 6/1979 | Yen et al. ................. 422/68 |
| 4,454,234 | 6/1984 | Czerlinski ................. 436/526 |
| 4,582,622 | 4/1986 | Ikeda et al. ................. 252/62.53 |
| 4,675,173 | 6/1987 | Widder ................. 436/806 |
| 4,795,698 | 1/1989 | Owen et al. ................. 435/4 |
| 4,879,220 | 11/1989 | Mrsny et al. ................. 436/525 |
| 4,920,061 | 4/1990 | Poynton et al. ................. 436/526 |
| 4,937,060 | 6/1990 | Kathirgamanathan et al. ........ 428/403 |
| 4,937,166 | 6/1990 | Creatura et al. ................. 428/407 |

*Primary Examiner*—James C. Housel
*Assistant Examiner*—Christopher L. Chin
*Attorney, Agent, or Firm*—Mary E. Gormley

[57] ABSTRACT

The invention relates to an aqueous suspension for diagnostic or immunodiagnostic tests, comprising non-polymer nuclei surrounded by a hydrophilic copolymer that contains functional groups, and also to a method for the preparation of this suspension. The method involves adding a monomer mixture to a colloidal dispersion of non-polymer particles, the monomer mixture being so chosen that the resultant copolymer has a charge of identical sign to that of the original dispersion. The invention also relates to a method for the detection of a specifically binding substance or immunochemically active component in a test fluid, and to a reagent and a test kit to be used when employing said detection methods.

3 Claims, 1 Drawing Sheet

METHOD FOR PREPARING AQUEOUS SUSPENSION FOR DIAGNOSTIC TESTS

This is a division of U.S. Ser. No. 07/865,773, filed Apr. 6, 1992, now abandoned, which is a file wrapper continuation of U.S. Ser. No. 07/731,373, filed Jul. 16, 1991, now abandoned, which is a file wrapper continuation of U.S. Ser. No. 07/434,965, filed Nov. 13, 1989, now abandoned.

The invention relates to an aqueous suspension for diagnostic or immunodiagnostic tests, comprising non-polymer nuclei surrounded by a hydrophilic copolymer that contains functional groups, and also to a method for the preparation of this suspension.

The invention also relates to a method for the detection of a specifically binding substance or immunochemically active component in a test fluid, and to a reagent and a test kit to be used when employing said detection methods.

The abovementioned suspension and a method for preparation of the suspension are known from U.S. Pat. No. 4,157,323. The particles of the suspensions described herein are microspheres consisting of a copolymer in which finely divided metal or metal oxide is embedded, as illustrated in FIG. 1.

In immunodiagnostic tests use is frequently made of proteins coupled to a label. Colloidal particles onto which the protein is physically adsorbed are then used as label. Disadvantages associated with this are, inter alia, the poor reproducibility of the preparation of the test material and leakage of protein. The meaning of the latter is that the active protein is not connected in a stable manner to the particles, as a result of which the test sensitivity decreases during storage.

The use of labels to which the proteins can be covalently bonded, as described in U.S. Pat. No. 4,157,323, can be a solution for problems of this type. In this case the non-polymer particles constitute the actual label. Label is understood to mean the component which can be detected by reason of a specific property (colour, radioactivity and the like).

The suspension from the abovementioned patent has several disadvantages. Firstly, the solid material in this suspension contains at most 50% by weight of non-polymer nuclei. This signifies a reduction in the test sensitivity and the number of application possibilities compared with labels with which protein is directly bonded to the nuclei. Secondly, a gold sol for the purpose of agglutination tests cannot be used in this suspension. However, gold particles form a very suitable label by virtue of the characteristic that the colour of a stable gold sol is red while the colour changes to blue on flocculating out (agglomeration of the particles in tests under the influence of the protein to be detected). When gold nuclei are used in the suspension according to U.S. Pat. No. 4,157,323 the colour of suspended particles is blue or red, but this colour cannot change on flocculating out.

When the particles are blue, the gold nuclei are embedded so closely to one another that there can already be considered to be agglomeration in each particle; see FIG. 2.

When the particles are red, the nuclei are separated from one another by the copolymer and will remain so even on agglomeration of the polymer spheres, as a result of which the colour does not change (see FIG. 3).

Moreover, this suspension also has a disadvantage in the use of dyestuff sols as nucleus. It is known from EP 0 032 270 that in the final detection of dyestuff sols the colour intensity can be intensified by allowing the sol particles to dissolve in an organic solvent. In the case of dyestuff particles embedded in the thick polymer shell of U.S. Pat. No. 4,157,323 this is, no longer possible.

The solid constituents of a suspension according to the invention have a content of non-polymer nuclei of at least 50% by weight and this suspension permits a colour change by agglomeration when gold nuclei are used. Moreover, the polymer which surrounds the nuclei is sufficiently thin to enable—via swelling—dissolution of dyestuff nuclei in an organic solvent.

The invention consists in that, in a suspension of the abovementioned known type, the non-polymer nuclei are each separately surrounded by their own shell of the copolymer. This is illustrated in FIG. 4.

Particles with this type of construction combine the advantages of the polymer surface with the characteristics of the nucleus in a ratio which is as favourable as possible. The content of non-polymer nuclei is dependent on the type of nucleus and the thickness of the polymer casing. In the case of gold this can be more than 90%. The thickness of the casing can vary from about 3 to about 70 nm depending, inter alia, on the experimental conditions.

Non-polymer nuclei are for example nuclei of metal, metal oxide, metal compounds, other inorganic compounds such as silica, organic dyestuffs or organic pigments and emulsion droplets of synthetic, animal, vegetable or mineral oils. Non-polymer nuclei which by virtue of a striking characteristic are best detectable are to be preferred. These are gold, by virtue of the already indicated colour change on agglomeration, hematite ($Fe_2O_3$) by virtue of the red-brown colour and magnetite ($Fe_3O_4$) by virtue of the magnetic properties.

When dyestuffs are used in colorimetric tests it is possible, with a correct choice of the dyestuff, to obtain a higher molar absorption—and thus a higher sensitivity—than with metal sols. Moreover—as mentioned above, an intensification of the colour can be obtained afterwards.

Copolymers which contain functional groups are understood as meaning copolymers which contain groups such as $OH$, $NH_2$, $COOH$, $CHO$, $SH$, $NN^+Cl^-$, to which proteins can bond directly or, after chemical treatment, covalently.

The invention also relates to a method for the preparation of the suspension according to the invention described above. With the known method according to U.S. Pat. No. 4,157,323, suspensions are prepared by in situ copolymerization of a mixture of monomers dissolved in water in the presence of non-polymer particles, the monomer mixture containing the following types of monomer:

an ethylenically unsaturated monomer which, without hydrolysis or after hydrolysis, contains at least one covalently bonding functional group;

a hydrophobic monomer;

a linking monomer.

With this method the non-polymer particles are dispersed in the monomer solution. In addition to the fact that the particles formed possess the disadvantages indicated above, the method also has several drawbacks. Thus, pure polymer spheres without a nucleus are also found to be formed. These are undesired by-products which must be removed. In addition, agglomeration of particles is found to be unavoidable. This is prevented by adding a stabilizer, for example a non-ionic surfactant. In labels for proteins a substance of this type in general disturbs the binding and the conformation of the proteins. When particles made according to a method of this type are used for immunodiagnostic tests separately added surfactants must be removed again. Frequently, however, this is only partly successful.

With the method according to the invention, the aim is to provide non-polymer particles with their own separate copolymer shell, it being possible to avoid the use of surfactants and no pure copolymer spheres being formed.

The characteristic of the method according to the invention is that a stable, colloidal dispersion of the non-polymer particles is used as starting material and that the monomer mixture is added to this, the monomer mixture being so chosen that the resultant copolymer has a charge of identical sign to that of the original dispersion.

The intended sign of the charge is determined by the electrophoretic mobility. This concept is known to those skilled in the art and requires no more detailed explanation here.

When the charges of the initial dispersion or emulsion and the shell polymer are not of identical sign, coagulation of the dispersion takes place during the formation of the shell in the absence of surfactants. Charges of identical sign are achieved by, during the polymerization, using an initiator which provides charged residual groups with a charge of the correct sign and/or using charged monomers with a charge of that sign.

The initial dispersion can be stabilized by peptizing ions, but also by weakly adsorbing surface active substances. Weakly adsorbing surfactants used in this stage can be removed well by means of microfiltration and do not hinder the use of the suspension in immunodiagnostic tests.

The ethylenically unsaturated monomers with at least one covalently bonding functional group can be chosen from monomers with an $OH$, $NH_2$, $COOH$, $CHO$, $SH$ or $NN^+Cl^-$ group. Examples of these are ethyleneimine, 2,3-dihydroxypropyl methacrylate, maleic acid, acrylamide, methylolacrylamide, (meth)acrylic acid, aldonic acid, allylamides such as arabinon allylamide, glucon allylamide, α-glucohepton allyamide, lactobion allylamide, sodium vinylsulphonate, methallyl sulphonate, dimethyl aminoethyl methacrylate, vinylpyridine salts, (meth)-acrylic acid esters of polyethylene glycol and vinylpyridine at low pH.

It is also possible to use monomers which after hydrolysis contain a covalently bonding functional group. Exampled of these are:

vinyl acetate (hydrolysis product: vinyl alcohol);

N-vinyl-tertiary butyl carbamate (hydrolysis product: vinylamine);

glycidyl methacrylate (hydrolysis product: 2,3-di-hydroxypropyl methacrylate); diethyl maleate (hydrolysis product: maleic acid).

The hydrophobic monomers can be chosen from monomers with a solubility in water of at least 35 g/l at 20° C. Examples of these are styrene, butadiene, butyl acrylate, vinylidene chloride, vinyl chloride, ethene, methyl methacrylate, ethyl acrylate, vinyl esters, diethyl maleate, glycidyl methacrylate and 2,3-epithiopropyl methacrylate.

The most advantageous hydrophobic monomers are, however, those which possess a hydrolysable group, so that a hydrophilic unit is formed in the polymer. Examples of these are the same hydrolysable monomers as described above.

Examples of linking monomers are N,N-methylenebisacrylamide, ethylene glycol dimethacrylate, diallyl phthalate, pentaerythritol triacrylate and N,N-diallyltartaric acid diamide. When monomers such as glycidyl methacrylate and methylol acrylamide which are already linkable are chosen as the hydrophilic and hydrophobic monomer, the addition of a separate linking monomer is superfluous. A linking agent is also not necessary when the copolymer is sufficiently insoluble in the polymerization medium. This is the case with a copolymer of styrene and acrylamide.

The ratio in which the monomers can be chosen is dependent on which monomers are chosen.

It is essential that the shell polymer formed possesses stabilizing properties. This can be demonstrated by allowing the monomer mixture to polymerize in the absence of the nucleus particles, while surfactants may also not be present. A copolymer which forms a stable latex with a particle size of between 50 and 300 nm now forms from suitable monomer mixtures.

A reagent or an immunochemical reagent also belongs to the invention. The term reagent signifies that the hydrophilic copolymer, which surrounds the non-polymer nucleus, is provided with a reactant.

Reactants which can be used are substances with which either a receptor or a ligand in a receptor-ligand combination can react. In such receptor-ligand combinations receptor and ligand have a direct or indirect bonding affinity for one another. Suitable receptor-ligand combinations are, for example, avidine-biotine or a DNA—DNA or DNA-RNA hybrids. The said reagent can then be used in a method for the detection of a specifically binding substance in a test fluid, this substance having a bonding affinity for the reactant present in the reagent.

The term immunochemical reagent signifies that the hydrophilic copolymer, which surrounds the non-polymer nucleus, is provided with an immunochemically active substance (as reactant). An antibody, an antigen or hapten can be used as immunochemically active substance.

This immunochemical reagent can then be used in a method for the detection of immunochemical active components in a test fluid. The immunochemical reaction which should take place when the detection method is used is preferably a sandwich reaction, an agglutination reaction, a competition reaction or an inhibition reaction.

In order, for example, to demonstrate an antigen in a test fluid, an antibody directed against the antigen can be bound to a suitable support, after which the test fluid is brought into contact with the support and the presence of immune complexes, formed between the antigen in the test fluid and the antibody, is detected by adding the suitable immunochemical reagent according to the invention to the support after the immune complex has formed.

Supports which can be used are, the inner wall of a microtest well, a tube or capillary, a membrane, filter, test strip or the surface of a particle, such as, for example, a latex particle, an erythrocyte, a dyestuff sol, a metal sol or metal compound as sol particle.

A test kit according to the invention must contain, as essential constituent, said reagent or immunochemical reagent.

The invention will be illustrated below with the aid of the following non-limiting examples and FIGS. 1 to 4 inclusive.

EXAMPLE 1

Figure 1:
FIG. 1 shows the particles of a suspension according to the prior art. Here various nucleus particles are embedded per particle.
Figure 2:
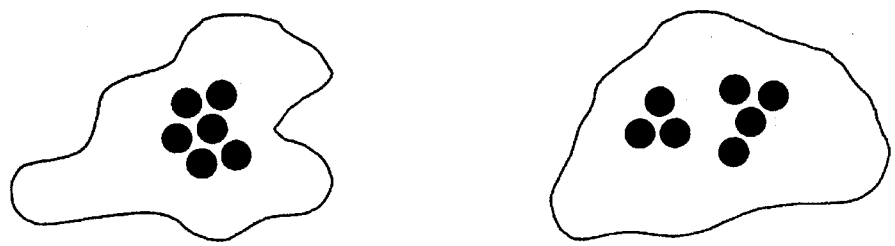
FIG. 2 shows particles of a suspension according to the prior art in which the nuclei are embedded close to one another.
Figure 3:
FIG. 3 shows particles of a suspension according to the prior art in which the nuclei are separated from one another by the copolymer.
Figure 4:
FIG. 4 shows the particles of a suspension according to the invention. In this case each nucleus possesses its own copolymer shell.

Coating of gold particles with a polymer shell

A gold seed sol with a particle size of about 20 nm is prepared by the method of Frens (Nature, Physical Sci. 241

(1973), 20). The gold sol has a solids content of 0.006% by weight. 80 ml of this sol are warmed to 70° C. in a double-walled, thermostat-controlled reactor at a stirring speed of 200 revolutions per minute. 0.1 g potassium persulphate and 0.06 g sodium bicarbonate dissolved in 5 ml distilled water are then added to the gold sol, followed by 7 ml of the following monomer solution:

2 g methyl methacrylate 1 g sodium vinylsulphonate 1 g N-methylenebisacrylamide 50 ml distilled water 50 ml methanol The mixture is stirred at 70° C. for 18 hours and then cooled to room temperature. The centrifuging tests show that no separate polymer particles have formed. Visible light absorption spectra show that no clusters of particles are present and that a polymer shell has formed. Dynamic light scattering tests and transmission electron microscopy show that the shell thickness is 77 nm.

EXAMPLE 2

Monomer mixture with hydrolysable hydrophobic monomer 2.1 Coating of gold particles with a thin polymer shell
Seed sol preparation A gold sol is prepared by reduction of a tetrachloroauric acid solution with sodium citrate according to the method described by Frens (Nature, Physical Sci. 241 (1973), 20). The solids content is 0.032% by weight gold. The mean particle size is 55 nm. The sol prepared in this way is colloidally stable without the addition of surfactants.
Coating procedure 800 ml of the seed sol are transferred to a thermostat-controlled 1-liter reactor and warmed to 70° C. with slow stirring (200 revolutions per minute, anchor stirrer). 10 ml of a solution of 0.32 g potassium persulphate and 0.2 g sodium bicarbonate in 50 ml distilled, deionized water are then added dropwise to the gold sol. 25 ml of a solution with the following composition is then added dropwise to the stirred, warm gold sol in the course of 1 hour:
Composition of monomer feed 0.75 g glycidyl methacrylate 0.38 g sodium vinylsulphonate 0.38 g N-methylenebisacrylamide 50 ml distilled water 50 ml methanol During the same period the remaining portion of the initiator/buffer solution is added. After adding the monomers and initiator, the mixture is stirred for a further 15 hours at 70° C. When the same experiment is carried out with water in place of the volume of gold sol a stable latex with a particle size of approximately 100 nm forms.
Characteristics of the coated gold sol 200 ml of the sol prepared in this way are purified by microfiltration with 6,000 ml distilled water. Analyses by transmission electron microscopy and quasi-elastic light scattering show that each individual gold particle is coated with an 11 nm-thick polymer shell. Less than 5% polymer particles without gold nucleus are formed. Each coated particle contains a single gold nucleus.

The purified, micro-filtered sol remains colloidally stable in a 0.2M sodium chloride solution in water, even after 60 hours. In contrast, the starting seed sol flocculates with a sodium chloride concentration of 0.04M.

The colour of the coated sol is virtually identical to that of the seed sol. Maximum absorption occurs at wavelengths of 539 and 533 nm. On flocculation, for example under the influence of sodium chloride, the characteristic colour change from red-pink to blue and finally grey-colourless is detected for both the seed sol and the coated sol.

2.2 Chemical, covalent bonding of immunoglobulin G (anti-human chorion gonadotrophin, a-hCG) to a polymer-coated gold sol
Introduction of aldehyde groups 100 ml of the encapsulated, micro-filtered gold sol from Example 2.1 are mixed with 8.7 ml of a 0.5M sodium periodate solution at pH=4.6.

The coated, micro-filtered gold sol mixed with 8.7 ml distilled water is taken as a blank experiment.

These mixtures are stored for 75 min at room temperature. The oxidation is then stopped by the addition of 304 ml ethylene glycol, after which the mixtures are stirred for a further 60 min. The sols are then micro-filtered with the 20-fold volume of distilled water.

Chemical binding of a-hCG 293A to the coated gold sol provided with aldehyde groups 100 ml of the gold sol provided with aldehyde functional groups are mixed with 5 ml of the buffered a-hCG solution (borate buffer, pH =9[a]). For comparison, the control (blank) is treated in the same way.

The mixtures are incubated at room temperature for 18 hours and then filtered through a coarse nylon filter.

These sols are then washed twice with tris buffer, pH=8[b] by centrifuging the sols for 60 min at 700 g.

The sediments are resuspended in tris buffer.

The coated gold sols which have been subjected to this treatment are tested for their immunological activity using a Predictor stick (Chefaro International). For this purpose 0.3 ml of conjugate (optical density=8.33) is mixed with 0.2 ml urine, containing 0, 50 and 1,000 International Units (I.U.) hCG/l respectively. A stick coated with monoclonal a-hCG (147B) is placed in the gold sol/urine mixture and incubated for 30 minutes at room temperature. The stick is then washed with water and the colour read off. The results are given below in Table I.

TABLE I

| Concentration hCG I.U./l | Control sol | Aldehyde sol |
|---|---|---|
| 0 | − | − |
| 50 | − | + |
| 1,000 | − | + |

− signifies no coloration visible on the stick
+ red-pink coloration visible on the stick a) borate buffer composition:
solution A: 0.2M boric acid+0.2M potassium chloride
solution B: 0.2M sodium carbonate
solution A is brought to pH=9.0 by adding solution B.
Buffered a-hCG solution: 1 part by volume a-hCG (9.9 mg ml⁻1) together with 8.4 parts by volume of the 0.2M borate buffer.
b) tris buffer composition:

0.25M tris (2-amino-2-(hydroxymethyl)-1,3-propanediol
0.25M sodium chloride
1.29 g bovine serum albumin/l
0.025 g thiomersal/l brought to pH=8 by adding concentrated hydrochloric acid.

2.3 Preparation of a thick polymer shell around individual gold particles
Coating The same procedure as described in Example 2.1 is chosen for coating the gold particles, except for the composition of the monomer feed.

| | |
|---|---|
| 1.70 g | glycidyl methacrylate |
| 0.85 g | sodium vinylsulphonate |
| 0.85 g | N-methylenebisacrylamide |
| 50 ml | distilled water |
| 50 ml | methanol |

200 ml of the sol thus obtained are micro-filtered with 6,000 ml distilled water and characterized. Using transmission electron microscopy a polymer shell thickness of a good 25 nm is estimated; from quasi-elastic light scattering a shell thickness of 40 nm is derived, which is an indication of the swelling of the polymer shell in water. The majority of the particles (>95%) are made up of a single gold nucleus surrounded by a polymer shell.

The coated, micro-filtered gold sol does not flocculate in 0.4M sodium chloride solution, even after 60 hours. Flocculation does occur at significantly higher sodium chloride concentrations, but the colour change, characterizing for the flocculation of uncoated gold sols, then no longer takes place. Instead, red-pink flocs are detected. If the seed gold sol is replaced by the corresponding volume of water, the polymerization of the monomers yields a stable latex with a particle size of a good 120 nm.

EXAMPLE 3

Coating of a dyestuff sol
3.1 Seed sol preparation 50 gram Palanil light red (a disperse dyestuff slurry BASF No. 7764060) are stirred in 1,000 ml distilled water for 45 minutes at room temperature. This dyestuff sol is purified by six successive washes with distilled water. The first 5 wash steps are carried out by centrifuging at an acceleration of 2,000 g for 30 min, followed by redispersion in distilled water. The final centrifuging step is carried out at an acceleration of 125 g for 60 min. This purification procedure is effective in removing surplus surfactant. Moreover, some fractionation occurs. The crude sol has a surface tension of 43.5 dyne/cm; the purified sol has a surface tension of 71.1 dyne/cm, both measured at a solids content of 4.8 g dyestuff/l.

3.2 Coating 125 ml dilute, washed dyestuff sol (0.145%) are warmed to 70° C. and stirred (200 rotations per minute) in a reactor. 12.5 ml of a solution of 0.10 g sodium bicarbonate and 0.10 g potassium persulphate in water are then added. 12.5 ml of a monomer solution of the following composition is then metered in with a peristaltic pump in the course of 1 hour:

| monomer feed | |
|---|---|
| 2 g | glycidyl methacrylate |
| 1 g | sodium vinylsulphonate |
| 0.5 g | N-methylenebisacrylamide |
| 50 ml | distilled water |
| 50 ml | methanol |

The composite sol is cooled after 16 hours and 100 ml were purified by microfiltration with 2,500 ml distilled water. The diameter of the coated sol is 86 nm larger than that of the initial sol, which is 316 nm. Centrifuging the composite sol in a 52 weight/weight % glucose/water solution with a density of 1.23 g/ml results in red particles sedimented on the bottom of the tube. No separate polymer particles are detected on the top of the supernatant liquor. With "sedimentation field flow fractionation" experiments also no separate polymer particles are detected.

The effect of the surface modification on the adsorption of proteins is substantial: two 4-ml tubes are filled with 1 ml uncoated, purified sol and 1 ml coated, purified dyestuff sol, respectively,. Each tube contains 0.054 g dyestuff. 1.75 ml phosphate buffer*) of pH=7.4 and then 0.75 ml of a solution containing 2.67 mg/ml bovine serum albumin (R-type, Organon Teknika) are added to these tubes.

*) Composition of phosphate buffer: solution A: 9.0772 g potassium dihydrogen phosphate in 1 liter of water; solution B: 11.8586 g disodium hydrogen phosphate in 1 liter of water; mix 5 parts of solution A with 24 parts of solution B.

The tubes are shaken at room temperature for 2 hours and then centrifuged. The bovine serum albumin content of the supernatant liquor is determined by HPSEC (high performance size exclusion chromatography). 0.28 mg/m$^2$ protein has been adsorbed on the uncoated, purified sol; no protein adsorption is detected on the coated sol.

3.3 Chemical, covalent bonding of immunoglobulin G (anti-human chorion gonadotrophin, a-hCG) to a polymer-coated dyestuff sol 3.3.1. Introduction of aldehyde groups.

The encapsulated, micro-filtered dyestuff sol from Example 3.2 and other samples with a different layer thickness in respect of the polymer coating are provided with aldehyde groups as described under 2.2.

3.3.2. Chemical bonding of a-hCG 293A to the coated dyestuff sol provided with aldehyde groups.

The coupling of a-hCG to the sols provided with aldehyde functional groups (see 3.3.1.) is carried out as described under 2.2.

3.4 Immunoassay.

The (a-hCG)-dyestuff sol conjugates made in this way are tested for their immunological activity in a sandwich immunoassay for hCG, as likewise described under 2.2, by incubating a a-hCG (147B) coated dipstick (Predictor stick; Chefaro International) at room temperature in a mixture of hCG-containing urine and conjugate (A1 cm/580 =8.3). The stick is then rinsed with water and the colour is read off. The results are given in Table II.

TABLE II

Dyestuff sol-(a-hCG) conjugates tested in a dipstick sandwich immunoassay for hCG (Predictor Stick, Chefaro International).

| Concentration hCG (I.U./l) | Incubation time (hours) | ACI-113* | ACI-124* | ACI-125* | ACI-126* | ACI-127* |
|---|---|---|---|---|---|---|
| 0 | 0.5 | − | − | − | − | − |
| 200 | 0.5 | +/− | +/− | − | − | − |
| 1,000 | 0.5 | + | + | +/− | − | − |
| 10,000 | 0.5 | + | + | + | +/− | +/− |
| 0 | 1.0 | − | − | − | − | − |
| 200 | 1.0 | +/− | +/− | +/− | − | − |
| 1,000 | 1.0 | + | + | + | +/− | − |
| 10,000 | 1.0 | + | + | + | + | + |
| 0 | 2.0 | − | − | − | − | − |
| 200 | 2.0 | +/− | + | +/− | − | − |
| 1,000 | 2.0 | + | + | + | +/− | +/− |
| 10,000 | 2.0 | + | + | + | + | + |

*)conjugate based on polymer-coated dyestuff sols with the following variable layer thickness (measured with the aid of dynamic light scattering/QELS):
ACI-113: 86 nm
ACI-124: 88 nm
ACI-125: 58 nm
ACI-126: 30 nm
ACI-127: 35 nm
+ red-pink colour visible on white stick
− no visible coloration of the white stick

EXAMPLE 4

The coating of gold particles above the solubility limit of the shell polymer 800 ml of the seed gold sol (0,032% by weight; see Example 1 for the preparation of this seed sol) are warmed to 70° C. in a thermostat-controlled reactor with reflux condenser and stirrer. 10 ml of a solution of 0.32 g potassium persulphate and 0.32 g sodium carbonate in 50 ml distilled water are added dropwise and 10 ml of a monomer solution of the following composition is added dropwise in the course of 1 hour:

| | monomer feed |
|---|---|
| 12 g | vinyl acetate |
| 4 g | diethyl maleate |
| 3 g | diethyltartaric acid diamide |
| 50 ml | water |
| 50 ml | methanol |

The remainder of the initiator/buffer solution is added during the addition of the monomers. 24 hours after the addition of the monomers the reactor is cooled to room temperature and the sol is purified by microfiltration with a 25-fold volume of water relative to the original sol volume. No polymer shell can be detected around the particles and the colloidal stability is just as low as that of the "uncoated" seed sol. Repetition of the polymerization procedure using water in place of the seed sol does not yield an insoluble polymer: the solution remains clear. However, if the polymerization procedure is carried out by adding not 10 ml but 80 ml of the above monomer solution in the course of 1 hour a latex is obtained with a particle size of 152 nm in the absence of seed sol. In the presence of gold particles a polymer shell is formed around the gold particles with a thickness of 27 nm. The colloidal stability is also distinctly greater than that of the seed sol.

EXAMPLE 5

Coating of gold particles below the solubility limit of the coating monomer 100 ml of a 0.032% by weight seed gold sol (for preparation see Example 1) are warmed to 70° C. under a blanket of nitrogen. 5 ml of a solution of 0.1 g potassium persulphate and 0.1 g sodium bicarbonate are added dropwise to this sol. 2.2 ml of a monomer solution with the following composition:

| | monomer feed composition |
|---|---|
| 5 g | styrene |
| 1 g | acrylamide |
| 80 ml | methanol | is then added with the aid of a peristaltic pump.

After stirring and warming to 70° C. for 24 hours, the reactor is cooled to room temperature. The gold sol is micro-filtered through a 25-fold volume of water. The purified sol proves able to withstand 0.10M sodium chloride after standing for 24 hours. No second generation of polymer particles has formed. Under these conditions styrene monomer dissolves completely in the reaction mixture.

When this polymerization is carried out without gold sol but with water in its place, a colloidal stable latex with a particle size of 120 nm is formed.

However, if a higher concentration of feed monomer is used by adding 3.4 ml of the following composition:

| | monomer feed |
|---|---|
| 10 g | styrene |
| 2 g | acrylamide |
| 80 ml | methanol | this yields a new generation of polymer particles. At this higher monomer concentration styrene monomer no longer dissolves in the mixture. Moreover, the gold particles treated in this way prove little able to withstand salt and after purification the sol already flocculates with 0.04M NaCl, the same concentration as the starting sol (seed sol). It can be concluded from this that in this case no polymer coating of the particles has taken place. In contrast to the gold particles, the newly formed polymer particles are able to withstand sodium chloride concentrations higher than 0.1M.

EXAMPLE 6

6.1 Comparison example analogous to US 4 157 323 Example 3

1.8 g hydroxyethyl methacrylate 0.3 g N-methylenebisacrylamide 0.6 g acrylamide 0.3 g methacrylic acid are dissolved in 90 ml deionized (Milli-Q) water in a double-walled reactor.

The solution is warmed to 70° C. and stirred at 200 rotations per minute. 0.1 g potassium persulphate and 0.1 g sodium bicarbonate dissolved in 10 ml water are then added.

After about 3–5 min large white flocs form. This indicates the formation of non-colloidal polymer.

6.2 Comparison example analogous to U.S. Pat. No. 4 157 323 Example 11

0.64 g hydroxyethyl methacrylate 0.70 g methyl methacrylate 0.64 g methacrylic acid 0.224 g ethylene glycol dimethacrylate are dissolved in 90 ml deionized (Milli-Q) water in a double-walled reactor.

Room temperature is chosen as the reaction temperature. 0.08 g potassium persulphate and 0.04 g sodium bisulphite dissolved in 10 ml of water are added to the mixture.

After 15 min an unstable latex (flocculated polymer) is detected.

I claim:

1. A method for the preparation of an aqueous suspension of particles of non-polymer nuclei each surrounded by a hydrophilic copolymer that contains covalent binding functional groups, comprising the steps of:

(1) adding an aqueous mixture of monomers to a colloidal dispersion of non-polymer particles; and (2) copolymerizing the monomer mixture, thereby forming an aqueous suspension of particles having non-polymer nuclei each surrounded by a hydrophilic copolymer shell containing said covalent bonding functional groups;

wherein said monomer mixture contains:

(a) an ethylenically unsaturated monomer that contains at least one of said covalent bonding functional groups or at least one group that can be hydrolyzed into a said covalent bonding functional group; and (b) a hydrophobic monomer that contains groups that are hydrolyzed to hydrophilic groups after the copolymerizing step (2); and wherein said monomer mixture is such that the resultant copolymer has a charge of identical sign to that of the original colloidal dispersion of non-polymer particles.

2. Method according to claim 1, wherein the monomer mixture comprises:

2 to 98% by weight glycidyl methacrylate, 0 to 96% by weight sodium vinylsulphonate and 2 to 40% by weight N, N-methylenebisacrylamide.

3. The method of claim 1, wherein the monomer mixture also contains a crosslinking monomer.

* * * * *